United States Patent [19]

Graham

[11] Patent Number: 5,780,028

[45] Date of Patent: Jul. 14, 1998

[54] METHOD OF OBTAINING IMMUNOGLOBULINS FROM COLOSTRUM AND THEIR USE IN PHARMACEUTICAL COMPOSITION

[75] Inventor: Conor John Graham, Victoria, Australia

[73] Assignee: Anadis Ltd., Australia

[21] Appl. No.: 617,750

[22] PCT Filed: Sep. 20, 1994

[86] PCT No.: PCT/AU94/00562

§ 371 Date: Mar. 18, 1996

§ 102(e) Date: Mar. 18, 1996

[87] PCT Pub. No.: WO95/08562

PCT Pub. Date: Mar. 30, 1995

[30] Foreign Application Priority Data

Sep. 20, 1993 [AU] Australia ............... PM 1313

[51] Int. Cl.$^6$ .......... A61K 39/395; A61K 39/42; B01J 13/00; B05D 3/00
[52] U.S. Cl. .......... 424/130.1; 424/147.1; 424/150.1; 424/151.1; 424/159.1; 424/164.1; 424/169.1; 424/809; 427/2.14; 427/2.16
[58] Field of Search .......... 424/150.1, 130.1, 424/147.1, 151.1, 159.1, 164.1, 169.1, 809; 427/2.14, 2.16

[56] References Cited

U.S. PATENT DOCUMENTS

| | | |
|---|---|---|
| 3,892,865 | 7/1975 | Roehm. |
| 4,051,235 | 9/1977 | Plymate. |
| 4,289,751 | 9/1981 | Windheuser. |
| 4,377,569 | 3/1983 | Plymate. |
| 4,863,875 | 9/1989 | Bailey et al. |
| 4,970,070 | 11/1990 | Raff. |
| 5,529,904 | 6/1996 | Ginsburg et al. |

FOREIGN PATENT DOCUMENTS

| | | |
|---|---|---|
| 34171189 | 11/1989 | Australia. |
| 8252791 | 2/1992 | Australia. |
| 0046909 | 6/1986 | European Pat. Off. |
| 190099 | 8/1986 | European Pat. Off. |
| 0102831 | 5/1989 | European Pat. Off. |
| 0391416 | 10/1990 | European Pat. Off. |
| 469359 | 2/1992 | European Pat. Off. |
| 0484148 | 5/1992 | European Pat. Off. |
| 222543 | 4/1991 | New Zealand. |
| 228595 | 11/1991 | New Zealand. |
| 1573995 | 9/1980 | United Kingdom. |
| 9308264 | 4/1993 | WIPO. |
| 9310818 | 6/1993 | WIPO. |

OTHER PUBLICATIONS

Ash et al Handbook of Industrial Chemical Additives VCH Publishers New York 1991 p. 480.

Sax et al Hawley's Condensed Chemical Dictionary Van Nostrand Reinhold Company New York 1987, p. 1038.

Muzik et al (Polia. Pharm. (Prague) (1984), 7, Abstract).

H. Hilpert, "Preparation of Milk Immunoglobulin . . . " Nestle Workshop Series vol. 5, pp. 17–28.

Y. Kanamaru, "Preparation of Various IGG Fractions from Bovine . . . " Res. Bull. Fac. Agr. Gifu Univ. vol. 57 pp. 165–174, 1992.

Parrott, E.L., "Compression", Pharmaceutical Dosage Forms, Tablets 2nd Ed., vol. 2, pp. 201–221, Marcel Dekker, Inc. New York, 1990.

Brandon et al., "The Mechanism of Transfer . . . " Australian Journal of Experimental Biology & Medical Science, (1971) V49, pp. 613–623.

Harlow et al. Antibodies—A Laboratory Manual (1988) Cold Spring Harbor Laboratory Press, pp. 298–300.

*Primary Examiner*—Anthony C. Caputa
*Assistant Examiner*—Mark Navarro
*Attorney, Agent, or Firm*—Ladas & Parry

[57] ABSTRACT

A pharmaceutical composition consisting, of nontoxic components wherein the nontoxic components comprise a core element comprising an antibody which binds to an antigen wherein the core element is a compressed tablet wherein compression forces used to prepare the tablet range from about 0.1 tonnes/cm$^2$ to about 42.1 tonnes/cm$^2$ and the process for preparing the composition.

13 Claims, 3 Drawing Sheets

ELISA Absorbance Readings

| | 0.075 mg/ml | 0.0375 mg/ml | 0.0187 mg/ml | 0.0094 mg/ml | 0.0047 mg/ml | 0.0023 mg/ml | 0.0012 mg/ml | 0.0006 mg/ml | 0.0003 mg/ml |
|---|---|---|---|---|---|---|---|---|---|
| Ave. Control | 0.17 | 0.113 | 0.065 | 0.047 | 0.028 | 0.01 | 0.017 | 0.007 | 0.012 |
| 9-5 | 0.179 | 0.11 | 0.075 | 0.045 | 0.019 | 0.002 | 0.001 | 0 | 0 |
| 10-10 | 0.168 | 0.119 | 0.067 | 0.035 | 0.02 | 0.001 | 0 | 0 | 0 |
| 11-20 | 0.139 | 0.094 | 0.047 | 0.024 | 0.015 | 0.005 | 0 | 0 | 0 |
| 12-40 | 0.139 | 0.088 | 0.038 | 0.01 | 0 | 0 | 0 | 0 | 0 |
| IgA Antibody | 0.34 | 0.301 | 0.253 | 0.209 | 0.147 | 0.096 | 0.064 | 0.047 | 0.032 |
| 13-60 | 0.155 | 0.105 | 0.062 | 0.031 | 0.017 | 0.011 | 0.007 | 0.013 | 0.009 |
| 14-80 | 0.156 | 0.102 | 0.055 | 0.038 | 0.021 | 0.017 | 0.006 | 0.01 | 0.049 |
| 15-100 | 0.164 | 0.108 | 0.071 | 0.038 | 0.024 | 0.01 | 0.003 | 0.005 | 0.003 |
| 16-120 | 0.157 | 0.102 | 0.048 | 0.032 | 0.014 | 0.018 | 0.002 | 0.001 | 0.002 |
| 17-140 | 0.164 | 0.106 | 0.067 | 0.029 | 0.017 | 0.016 | 0.005 | 0.004 | 0.01 |
| 18-160 | 0.175 | 0.092 | 0.072 | 0.035 | 0.014 | 0.005 | 0.005 | 0 | 0.004 |

PUNCH TIP PRESSURE EQUIVALENTS FOR 7 MM FLAT FACE PUNCH IN TONNES (1000 KG) PER CM SQUARE

| | | | | | | | | | | |
|---|---|---|---|---|---|---|---|---|---|---|
| Force | kN | 5 | 10 | 20 | 40 | 60 | 80 | 100 | 120 | 140 | 160 |
| | Tonnes | 0.5 | 1 | 2 | 4 | 6 | 8 | 10 | 12 | 14 | 16 |
| Pressure | Tonnes/cm$^2$ | 1.3 | 2.6 | 5.2 | 10.5 | 15.7 | 21.0 | 26.3 | 31.5 | 36.8 | 42.1 |

METHOD OF OBTAINING IMMUNOGLOBULINS FROM COLOSTRUM AND THEIR USE IN PHARMACEUTICAL COMPOSITION

This application is a continuation of the national phase of PCT/AU94/00562, filed Sep. 20, 1994.

The present invention relates to a pharmaceutical composition, in particular a pharmaceutical composition including antibodies and to a method of preparing same.

BACKGROUND OF THE INVENTION

It is known that antibodies may be separated from human blood and used to treat various infectious diseases. In particular γ-globulin fractionated from blood serum has been known to have effectiveness in treatment and prophylaxis of disease and was administered by injection in the treatment of measles and other infectious diseases. It was later found that in fact, γ-globulin and part of the β-globulin fraction were composed of five major constituents: IgG, IgA, IgM, IgD and IgE, each of which has its own physiological characteristics. However, such serum antibodies are difficult to collect, with the result that commercial production of large quantities of antibodies for medication is not economical. It was found that IgA was produced not only in blood serum but also in secretory organs such as the mammary gland. The IgA found in the secretory organs is in the form of a dimer consisting of two molecules of IgA, which are bridged with one molecule of a secretory component. This form of IgA is very stable against proteases and acidic conditions and is known as secretory IgA as distinguished from serum IgA. Unlike other immuno globulins, IgA present in the form of secretory IgA in the epithelial cells of mucous membranes attacks bacteria and viruses therein, thus playing an important role in local immunity. Because of this, oral administration of secretory IgA may be used to provide immunological protection to a patient, and it is known that this occurs naturally from the inferior resistance against infection exhibited by a bottle-fed infant as opposed to a breast-fed infant.

Secretory IgA is found in particularly high concentrations in colostrum. Colostrum is milk produced by mammals over a period extending from shortly before to shortly after giving birth. Colostrum contains on average 300 mg/dl secretory IgA, compared with 50 mg/dl for mature milk. It is recognized that by immunizing a mammal such as a cow with specific antigens, a colostrum containing specific antibodies may be harvested and used to treat infectious diseases, particularly intestinal diseases. For many applications, this has proved a preferable commercial alternative to isolating γ-globulin from blood serum.

Although colostrum has proved a useful source of secretory IgA, difficulties have been experienced in the purification and storage of colostral antibodies. In particular, it has been found that colostral antibodies isolated by previously known methods may not be sufficiently stable to withstand some of the conditions found during the preparation and storage of pharmaceutical compositions, or the physiological conditions which may be encountered by a pharmaceutical composition prior to reaching the intended site of activation.

A further problem is found in the administration of colostral antibodies. Previously, colostral antibodies have been administered in compositions including a large percentage of pharmaceutically acceptable excipients. This in turn has resulted in impractical dosing due to the large quantities of pharmaceutical composition required to achieve desired levels of antibody administration. Prior art methods have included powders which may be dissolved or suspended in liquid for oral administration, or granulation and encapsulation of colostral antibodies, again for oral administration. Both of these methods require high dosage level regimes to ensure effective levels of antibodies are received.

Administration is also complicated by the origin of the antibodies. Since it is derived from milk products, quantities of lactose are often associated with the separated antibodies. This results in an increase in the overall volume of pharmaceutical compositions including the antibody, and makes the compositions unsuitable for administration to individuals who are lactose intolerant.

SUMMARY OF THE INVENTION

It is accordingly an object of the present invention to overcome, or at least alleviate, one or more of the difficulties raised in the prior art.

Surprisingly, it has been discovered that it is possible to compress colostral antibodies collected and purified according to the method of the present invention, into a tablet form without substantial loss of activity. This is contrary to the accepted view, which holds that the forces necessary to create a compressed tablet would denature and destroy any antibodies present in the tablet.

BRIEF DESCRIPTION OF THE FIGURES

FIG. 2 shows ELISA adsorbance readings obtained from testing of immunological activity of compressed antibodies and antibody powder which was not subjected to compression.

FIG. 3 shows punch tip pressure equivalents for 7 mm flat face punch.

DETAILED DESCRIPTION OF THE INVENTION

Figure 1:
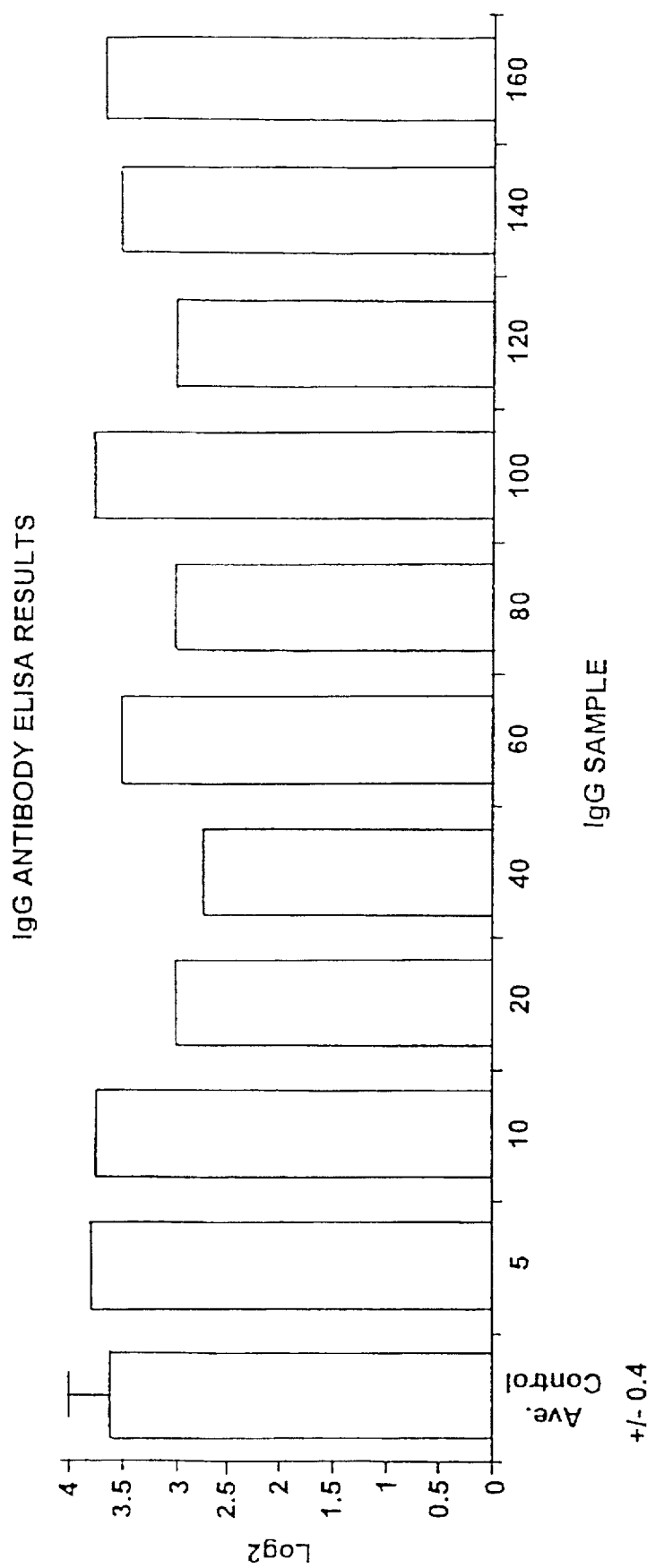
FIG. 1 shows the immunological activity of compressed antibodies and antibody powder which was not subjected to compression.

Accordingly, in a first aspect of this invention, there is provided a method of obtaining a high purity immunoglobulin preparation from an antibody rich colostrum, which includes:

(i) removing milk fat from the colostrum to obtain a low-fat colostrum;

(ii) pasteurizing the low-fat colostrum;

(iii) coagulating the pasteurized, low-fat colostrum and removing milk curd containing casein;

(iv) centrifuging remaining liquid to remove precipitates;

(v) removing lactose, minerals and water to obtain an antibody containing fraction;

(vi) dissolving the antibody containing fraction in TRIS-HCl buffer and dialyzing against the same buffer; and vii) concentrating the antibody containing solution to obtain a 10% by weight antibody solution.

The immunoglobulin preparation may then be preserved by snap freezing and freeze drying the antibody solution.

The removal of lactose, minerals and water in step (v) may be carried out by any process known in the art such as reverse osmosis or ultrafiltration. Preferably, saturated ammonium sulphate solution is added to the supernatant obtained in step (iv) to precipitate a antibody containing fraction and the resulting mixture is centrifuged. The supernatant containing the lactose, minerals and water is then discarded.

The buffer in step (vi) is preferably a 0.01 M TRIS-HCl buffer at pH 8, and contains 0.32 M Na Cl. The immunoglobulin-buffer solution is preferably dialyzed against approximately 5 times by volume of the same buffer and may be dialyzed using any known apparatus. Preferably an Amicon spiral membrane system or hollow fiber method is used. Specific colostral antibodies may be obtained by immunizing a mammal from which colostrum is collected, with specific antigens. Preferably the animal immunized is a cow. For example, the immunoglobulin preparation of the present invention may contain specific antibodies against enterotoxic bacteria such as *Escherichia coli, Salmonella, Shigella, Vibrio cholera*, protozoan cryptosporidium, enterotoxic viruses and against specific toxins.

The immunoglobulin preparation obtained according to the above method may have improved stability as well as high purity.

In a second aspect of this invention, there is provided a pharmaceutical composition including A core element including an active antibody component, preferably obtained from colostrum; wherein the core element is in the form of a tablet, preferably in the form of a compressed tablet. The compression forces used to prepare the tablet are such that they do not injure or denature the active antibodies. Preferably the compression forces are between about 0.1 tonnes/cm$^2$ and 42.1 tonnes/cm$^2$; more preferably between about 1.3 tonnes/cm$^2$ and 10.5 tonnes/cm$^2$; more preferably about 8 tonnes/cm$^2$.

The core element of the present invention may contain a mixture of antibodies for concurrent administration. The core element may also contain other active ingredients such as: antihistamines, antibiotics, antituberculous agents, cholineigic agents, antimuscarinics, sympathomimetics, sympatholytic agents, autonomic drugs, iron preparations, haemostatics, cardiac drugs, antihypertensive agents, vasodilators, nonsteriodal anti-imflammatory agents, opiate agonists, anti convulsants, tranquilizers, stimulants, barbituates, sedatives, expectorants, antiemetics, gastrointestinal drugs, heavy metal antagonists, antithyroid agents, genitourinary smooth muscle relaxants and vitamins.

It is preferred that the core element of the present invention contain approximately 20 to 90% by weight, preferably 40 to 80% by weight of active antibodies derived from colostrum. The remainder of the core element may include other active ingredients as discussed above and may further include pharmaceutically acceptable carriers or excipients, fillers, stabilizing agents, plasticizers, surfactants lubricants, effervescent agents, binders and colorents.

Suitable fillers may be selected from insoluble materials such as silicon dioxide, talc, titanium dioxide, alumina, starch, kaolin, polacrilin potassium, powdered cellulose, microcrystaline cellulose, AMYLOPECTIN N (trademark) (amylopectin) Synthetic silicas such as AEROSIL (trademark silica), SIPERNAT 22 (trademark silica), and SIPERNAT 22 S (trademark), and mixtures thereof and soluble fillers selected from manitol, sucrose, lactose, dextrose, sodium chloride, sorbitol and mixtures thereof.

The binding agent may be selected from polyvinyl pyrrolidone, hydroxypropyl cellulose, hydroxypropyl methyl cellulose, methyl cellulose, hydroxyethyl cellulose, carboxymethyl cellulose, sugars and mixtures thereof.

The effervescent agents are preferably a mixture of citric acid and sodium bicarbonate. Magnesium stearate may be added In a preferred form of the invention, the core element is provided with an enteric coating. The enteric coating is insoluble in acidic media but soluble in neutral or alkaline media such that the enteric coating protects the tablet and enables the tablet to manifest its pharmacological activity in the intestine. The enteric coating may be any of the enteric coatings known in the art. Such coatings include cellulose acetate phthalate, hydroxypropyl methyl- cellulose phthalate, hydroxpropyl methyl-cellulose acetate succinate, methacrylic acid copolymer, shellac cellulose acetate trimellitate and mixtures thereof. A particularly preferred enteric polymer is sold under the trade name EUDRAGIT L 100-55 and is a methacrylic acid:acrylic acid ethylester 1:1 copolymer.

In a further embodiment of the invention, the enteric coating may be adapted to provide sustained release of active ingredients contained in the core element. In such an embodiment, the enteric coating may also contain at least one partially acid-soluble component selected from polymers such as polyvinyl pyrrolidone, hydroxypropyl cellulose, hydroxy propylmethyl cellulose, polyethyleneglycol, polyvinyl alcohol and monomers thereof such as sugars, salts or organic acids and mixtures thereof. The enteric coating may also contain at least one insoluble matrix polymer selected from ethyl cellulose, acrylic and/or methacrylic ester polymers or mixtures thereof.

The partially acid-soluble component may be present in the enteric coating in amounts from approximately 1 to 60%, preferably 15 to 40%, more preferably 20 to 35% by weight based on the total weight of the enteric coating excluding the weight of any filler or plasticizer. The insoluble matrix polymer may be present in the enteric coating in an amount from approximately 1 to 85%, preferably 35 to 75%, more preferably 45 to 65% by weight based on the total weight of the enteric coating excluding the weight of any filler and plasticizer.

Plasticizer may be present in the enteric coating preferably in the amount of 0 to 50% by weight based on the total weight of the enteric coating. The plasticizer may be selected from cetyl alcohol, diethyl phthalate, triethyl citrate, triethyl acetyl citrate, triacetine, tributyl citrate, polyethylene glycol and glycerol and the like. The selection of plasticizer will largely be dictated by the polymer used in the enteric coating and the compatability of the plasticizer with the coating solution or dispersion.

A filler may be present in an amount of 0 to 75% by weight based on the total weight of the enteric coating. A filler may be selected from insoluble materials such as silicane dioxide, titanium dioxide, talc, alumina, starch, kaolin, powdered cellulose, and microcrystaline cellulose and mixtures thereof.

In a further aspect of this invention, there is provided a process for preparing a pharmaceutical preparation including a core element including an immunoglobulin preparation derived from colostrum which process includes:

(a) providing an antibody rich colostrum, (b) isolating, an immunoglobulin preparation from the colostrum, and (c) forming a core element from said immunoglobulin preparation.

The core element produced by the process is preferably a tablet, more preferably a compressed tablet. The compressed tablet is formed using compression forces such that they do not injure or denature active antibodies.

In a particularly preferred embodiment, the core element is given an enteric coating. This may be done by conventional means such as spraying the coating onto the core element in a pan coater. Preferably, the coating comprises 2 to 5% by weight of the pharmaceutical preparation. Suitable enteric coating compositions may include any of the compounds previously described in that regard.

The present invention will now be more fully described with reference to examples. It should be understood, however, that the description following is illustrative only, and should not be taken in any way as a restriction on the generality of the invention described above.

EXAMPLE 1

Production of Antibodies

Two dairy cows were immunized with a mixture of enterotoxigenic E. coli representing somatic sero groups O8 and O15 associated with traveller's diarrhoea. Bacteria were heat inactivated and a suspension of 2 billion organisms in 2 ml of physiological saline was emulsified with the same volume of Montanide ISA 70 adjuvant. The resulting vaccine was administered weekly during the last 8 weeks of gestation.

Isolation and Purification of Antibodies

Colostral milk was collected during the first two days of lactation. The milk fat was removed and skim milk was pasturized at 56° C. for 30 minutes and then coagulated by renetting as in Hilpert, Human Milk Banking 1984. After removal of milk curd containing caseine, the whey was centrifuged and the fine precipitate was disgarded.

An equal volume of saturated ammonium sulfate solution was slowly added to the supernatant with continuous mixing as in Brandon et al, Aust. J. Exp. Biol. Med. Sci., 1971, V 49, p613. After centrifugation the resulting precipitate was saved and the supernatant containing lactose and salts was discarded.

The precipitate was dissolved in 0.01M TRIS-HCl buffer pH8 containing 0.32M NaCl (30% of original volume). This solution was extensively dialyzed against five volumes of the same buffer using an Amicon spiral membrane SIY30 cartridge. The antibody solution was then concentrated to 10%, snap frozen and freeze dried.

Preparation of Antibody Tablets

The freeze dried antibody powder was formulated into highly soluble tablets each weighing 500 mg. Each tablet comprised as follows:

| Colostral Antibodies | 80% |
|---|---|
| Microcrystalines cellulose | 6% |
| Carboxymethyl cellulose | 3.2% |
| Citric acid | 6% |
| Sodium bicarbonate | 6% |
| Magnesium sterate | 0.8% |

All ingredients were blended as a dry mix in a conical mixer before compression. Resulting powder mixture was compacted using a roller compactor. A granulation was compressed on a single stroke Manesty tableting machine.

Enteric Coating

An enteric coating comprising a water based dispersion of EUDRAGIT L 100-55 polymer with 3% cetyl alcohol (w/w) as plasticizer was sprayed onto the tablets in a conventional pan coater to provide a uniform coating. Sufficient coat integrity is achieved by using 2 to 5% of coating mixture (w/w).

Testing

The coated tablets were subjected to disintegration tests and were dissolved within 9 to 12 minutes in pH 6.5 and within 5 to 9 minutes in pH 8.

Antibody activity in the antibody granulation before compression into tablets was compared with the antibody activity in the uncoated and the coated antibody tablets. The granulation, the uncoated tablet and the coated tablet were dissolved separately in 100 ml of phosphate-saline buffer pH 8. The antibody titers in the three solutions were compared using ELIZA assay. The ELIZA plates were coated overnight with a suspension of bacteria used for vaccination. The plates were then processed in the standard manner to test the serial dilutions of antibody solutions. The antibody titers were similar for all three solutions indicating full preservation of antibody activity in the compressed and enterically coated tablets.

EXAMPLE 2

Compression of Colostral Antibodies
Antibodies

Colostral antibodies against E. Coli K88 were isolated and purified according to the method of Example 1. Formulation of antibodies for the compression test The antibodies were pulverized by a pin roller and sieved through 30 mesh screen. The resulting antibody powder was added to the mixing vessel containing 0.5% w/w SIPERNAT 22 S (silica). After thorough mixing (5 minutes) 13.5% w/w SIPERNAT 22 (silica) and 8.5% w/w of AMYLOPECTIN N were added and blended with antibody powder for a further 5 minutes. Finally 0.5% w/w of magnesium stearate was added and blended for 2 minutes. The resulting tableting mix had the following formulation used in the compression test:

| Antibody powder | 77% wt |
|---|---|
| SIPERNAT 22 (silica) | 13.5% wt |
| AMYLOPETIN N | 8.5% wt |
| SIPERNAT 22 S (silica) | 0.5% wt |
| Mg Stearate | 0.5% wt |

Compression Test

The compression test used a custom built compression apparatus using a custom built die and punch set. Five tablets were produced at designated pressure levels. The whole die and punch assembly containing tableting powder was placed inside a holding frame of the compression apparatus. A force ranging from 5 to 160 kiloNewtons (kN) was applied to the upper punch by means of a hydraulic ram. The working surface of the ram was 73.1 cm$^2$ and the surface of the punch tip was 0.38 cm$^2$. The range of punch tip pressures transferred to the tablets ranged respectively from 1 300 to 42 100 kg per cm$^2$.

Preparation of compressed tablets for evaluation of immunological activity

Three tablets from each of the pressure points set out in FIG. 3 were ground in mortar and pestle to a fine powder. One hundred milligrams of the powder was transferred to the test tubes and 10 mL of phosphate-saline buffer, pH 7.2 was added. One hundred milligrams of the tableting mix in a powder form which had not been compressed served as a control. The test tubes were placed on a Coulter Mixer and antibodies extracted overnight at room temperature. After extraction, the test tubes were centrifuged at 3000 rpm for 1 hour and the aliquots of the supernatants were assayed for antibody activity using ELISA test.

ELISA assay for determination of antibody activity against E. coli.

The Elisa assay was performed essentially as described by Voller A. at al. (1980) Enzyme linked immunosorbent assay. In Manual of Clinical Immunology, pp. 359–371. Eds N. R. Rose & H. Friedman. American Society for Microbiology, Washington, D.C. Modifications of the assay were introduced to measure antibody activity against *E. coli* K 88 antigen.

Briefly, 100 µl suspension of a $10^9$ K 88 *E. coli* in carbonate buffer (0.1M, pH 9.6) was placed in each well of a flat-bottom Nunc Polysorb plate and incubated overnight at 4° C.

The plates were washed three times with PBS/Tween buffer (0.1M PBS and Tween 20, 0.05% v/v).

After the washes the treatment of the plates consisted of subsequent 1 hour incubations with 100 ul/well of reagents diluted in working buffer (PBS/Tween buffer to which 0.25% w/w of BSA had been added) were used in following order with 3 washes each in between:

(1) test antibodies diluted 1:100 in working buffer were serially diluted across the plate.

(2) Peroxidase-conjugated, rabbit anti-bovine immunoglobulins (Sigma,US) 1:1000 dilution in working buffer.

Finally, substrate solution containing citrate buffer (96 ml), hydrogen peroxide (2 ml of 126 ul 30% hydrogen peroxide in 10 ml distilled water), ABTS® (2 ml) was added to each well. After 2.5 hours the plates were scanned for absorbance at 4.4 nm.

Results

The investigation evaluated the effect of compressing pressure on the immunological activity of colostral antibodies. The tableting mix containing 77% of antibody powder and 23% disintegrants and other excipients was compressed over the range of pressures from 1.3 to 42.1 tonnes per $cm^2$. All antibody samples including the control were tested in the same ELISA assay.

The results of the investigation are presented in FIG. 1 and FIG. 2. FIG. 1 is a bar graph comparing the immunological activity of compressed antibodies with the control antibody powder which was not subjected to compression. FIG. 2 contains raw data of ELISA absorbance readings. The average Log transformed value of the control sample (the antibody powder not subjected to compression) was 3.62±0.4 and the average for all comprised samples was 3.37±0.6.

Conclusion

The final pressure 42.1 tonnes per $cm^2$ exceeded more than five times the maximum allowable pressure for commercial equipment. Surprisingly the immunological activity of colostral antibodies was preserved over the whole range of pressures tested. These results indicate that the colostral antibodies formulated as described herein may be tableted without significant loss of immunological activity.

It is to be understood that various other modifications and/or alterations may be made without departing from the spirit of the invention as outlined herein.

I claim:

1. A pharmaceutical composition consisting of nontoxic components wherein said nontoxic components comprise a core element comprising an antibody which binds to an antigen wherein the core element is a compressed tablet wherein compression forces used to prepare the tablet range from about 0.1 tonnes/$cm^2$ to about 42.1 tonnes/$cm^2$.

2. A pharmaceutical composition according to claim 1 wherein the core element comprises about 20 to 90% by weight of antibodies.

3. A pharmaceutical composition according to claim 1 wherein the core element is provided with an enteric coating.

4. A pharmaceutical composition according to claim 1 wherein the antibody is obtained from colostrum.

5. A pharmaceutical composition according to claim 1 wherein the core element comprises one or more antibodies selected from antibodies against enterotoxic bacteria, protozoan, crypotosporidium, enterotoxic viruses or toxins.

6. A pharmaceutical composition according to claim 1 wherein the antibodies against enterotoxic bacteria are antibodies against *Escherichia coli*, *Salmonella*, *Shigella*, or *Vibrio cholera*.

7. A pharmaceutical composition according to claim 1 wherein the core element further comprises active ingredients selected from the group consisting of antihistamines, antibiotics, antituberculous agents, cholinergic agents, antimuscarinics, sympathomimetics, sympatholytic agents, autonomic drugs, iron preparations, haemostatics, cardiac drugs, antihypertensive agents, vasodilators, nonsteroidal anti-inflammatory agents, opiate agonists, anti convulsants, tranquilizers, stimulants, barbiturates, sedatives, expectorants, antiemetics, gastrointestinal drugs, heavy metal antagonists, antithyroid agents, genitourinary smooth muscle relaxants and vitamins.

8. A pharmaceutical composition according to claim 1 wherein the core element further comprises fillers selected from the group consisting of silicon dioxide, talc, titanium dioxide, alumina, starch, kaolin, polacrilin potassium, powdered cellulose, microcrystalline cellulose, amylopectin, synthetic silicas, manitol, sucrose, lactose, dextrose, sodium chloride, sorbitol or mixtures thereof.

9. A pharmaceutical composition according to claim 1 wherein the core element further comprises a binding agent selected from polyvinyl pyrrolidone, hydroxypropyl cellulose, hydroxypropylmethyl cellulose, methyl cellulose, hydroxyethyl cellulose, carboxymethyl cellulose, sugars or mixtures thereof.

10. A pharmaceutical composition according to claim 1 wherein the core element further comprises a mixture of citric acid and sodium bicarbonate as an effervescence agent.

11. A pharmaceutical composition according to claim 1 wherein the core element comprises:

| | |
|---|---|
| Antibodies | 77% wt. |
| precipitated, spray dried silica | 13.5% wt. |
| amylopectin | 8.5% wt. |
| precipitated, ground, spray dried silica | 0.5% wt. and |
| Magnesium Stearate | 0.5% wt. |

12. A pharmaceutical composition according to claim 1 wherein the compression forces used are in the range from about 1.3 tonnes/$cm^2$ to about 42.1 tonnes/$cm^2$.

13. A process for preparing a pharmaceutical composition consisting of nontoxic components wherein said nontoxic components comprise a core element comprising an antibody which binds to an antigen said process comprises providing a tableting powder containing antibodies which bind to antigens and compressing the tableting powder using a force of between about 0.1 tonnes/$cm^2$ and about 42.1 tonnes/$cm^2$ to form a tablet.

* * * * *